(12) United States Patent
Broz et al.

(10) Patent No.: US 8,912,795 B2
(45) Date of Patent: Dec. 16, 2014

(54) NUCLEAR MAGNETIC RESONANCE SCANNING OF METAL CONTAINERS USING MEDIUM-FIELD TECHNOLOGY

(75) Inventors: Joseph S. Broz, Alexandria, VA (US); Stephen W. Surko, Chevy Chase, MD (US)

(73) Assignee: Wine Scanner Inc., Hamburg, NJ (US)

( * ) Notice: Subject to any disclaimer, the term of this patent is extended or adjusted under 35 U.S.C. 154(b) by 467 days.

(21) Appl. No.: 13/306,291

(22) Filed: Nov. 29, 2011

(65) Prior Publication Data
US 2012/0133358 A1 May 31, 2012

Related U.S. Application Data

(60) Provisional application No. 61/418,397, filed on Nov. 30, 2010.

(51) Int. Cl.
*G01V 3/00* (2006.01)
*G01N 24/08* (2006.01)
(52) U.S. Cl.
CPC ................................. *G01N 24/084* (2013.01)
USPC ........................................................ 324/309

(58) Field of Classification Search
USPC .................................................. 324/300–322
See application file for complete search history.

(56) References Cited

U.S. PATENT DOCUMENTS

| | | | |
|---|---|---|---|
| 6,456,072 B1 * | 9/2002 | Webb et al. ................. | 324/308 |
| 6,794,865 B2 * | 9/2004 | Astley et al. ............... | 324/306 |
| 7,355,402 B1 * | 4/2008 | Taicher et al. ............. | 324/300 |
| 7,688,069 B2 * | 3/2010 | Kraus et al. ................ | 324/309 |
| 8,019,466 B2 * | 9/2011 | Ewing et al. ............... | 700/225 |
| 8,242,779 B2 * | 8/2012 | Blumich et al. ............ | 324/309 |
| 8,390,286 B2 * | 3/2013 | Matlashov et al. ......... | 324/309 |
| 8,456,164 B2 * | 6/2013 | Subbarao ................... | 324/309 |
| 2010/0090698 A1 * | 4/2010 | Blumich et al. ............ | 324/309 |
| 2010/0219827 A1 * | 9/2010 | Matlashov et al. ......... | 324/307 |

FOREIGN PATENT DOCUMENTS

| | | | | |
|---|---|---|---|---|
| EP | 1947449 A1 * | 7/2008 | ............ | G01R 33/44 |
| WO | WO 2011112743 A1 * | 9/2011 | | |

* cited by examiner

*Primary Examiner* — Dixomara Vargas
(74) *Attorney, Agent, or Firm* — Baker & Hostetler LLP

(57) ABSTRACT

A method and apparatus are provided for medium-field NMR scanning of liquids that is capable of discriminating benign liquids such as lotions, drinks, and pharmaceutical liquids from threat liquids such as components of home-made explosives.

20 Claims, 9 Drawing Sheets

NUCLEAR MAGNETIC RESONANCE SCANNING OF METAL CONTAINERS USING MEDIUM-FIELD TECHNOLOGY

CROSS REFERENCE TO RELATED APPLICATIONS

This application claims priority to provisional U.S. patent application entitled "Nuclear Magnetic Resonance Scanning of Metal Containers Using Medium-Field Technology," filed Nov. 30, 2011, having Ser. No. 61/418,397, the disclosure of which is hereby incorporated by reference in its entirety.

GOVERNMENT RIGHTS

This invention was made with government support under contract No. HSHQDC-08-C-00180 awarded by the Department of Homeland Security (DHS). The government has certain rights in the invention

BACKGROUND OF THE INVENTION

Nuclear Magnetic Resonance (NMR) has been used for testing for the presence of various components in substances, including testing of consumables such as food and beverages in closed containers. See, e.g., U.S. Pat. Nos. 6,911,822, 7,012,427, and 7,339,377. Other patents relevant to NMR testing of substances to determine the presence of various components include U.S. Pat. Nos. 3,975,675, 4,045,723, 4,550,082, 5,270,650, 5,530,353, 5,811,305, 6,333,629, 6,462,546, and 6,806,090. Non-patent references include Weekley, A. J., et al., "Using NMR to Study Full Intact Wine Bottles," J. Magn. Reson., 161:91-98 (2003); Sobieski. D. N., et al., "Towards Rapid Throughput NMR Studies of full Wine Bottles," Solid State NMR, 29:67-74 (2006); Drysdale and Fleet "Acetic Acid Bacteria in Winemaking: A Review" Am. J. Enol. Vitic. 39:143-154 (1988); Castilieira et al. "Simultaneous Determination of Organic Acids in Wine Samples by Capillary Electrophoresis and UV Detection: Optimization with Five Different Background Electrolytes" J. High Resol. Chromatogr. 23:647-652 (2000); Guillou and Reniero "Magnetic Resonance Out Bad Wine" Physics World 11:22-23 (1998); Hayes et al. "An Efficient, Homogeneous Radiofrequency Coil for Whole-Body NMR Imaging at 1.5 T" J. Magn. Reson. 63:622-628 (1985); Schindler et al. "A Rapid Automated Method for Wine Analysis Based Upon Sequential Injection (SI)-FTIR spectroscopy" Fresenius 362:130-136 (1998); Weekley, A. J., Bruins, P. And Augustine, M. P., "Nondestructive Method Of Determining Acetic Acid Spoilage In An Unopened Bottle Of Wine" American Journal Of Enology And Viticulture, Vol. 53, December 2002 (2002-12), Pages 318-321; Mccarthy And Kauten Magnetic Resonance Imaging Applications In Food Research "Trends In Food Science And Technology, 1990, Pages 134-139; Schmidt, Sun And Litchfield, Applications Of Magnetic Resonance Imaging In Food Science" Critical Reviews In Food Science And Nutrition, Vol. 36, No. 4, 1996, pages 357-385.

There is a prevailing operational need for a unified, cost-effective approach to the detection of liquid explosive threats in the civil aviation industry as well as other mass transportation modes, such as a tabletop Bottled Liquid Scanner (BLS) that is capable of detecting and distinguishing threat liquids from benign liquids in unopened/sealed Stream-of-Commerce (SOC) containers including non-ferrous metal containers.

Nuclear relaxometry methods at ultra-low fields (ULF) using extremely sensitive sensors haven been used to measure relaxation parameters that enable the gross differentiation of liquids. Relaxation time data set pairs (denoted $T_1$ and $T_2$) can be used to generally characterize certain (protonated) liquids.

Several significant technical issues remain to be resolved with low-field relaxometry approaches, including accurate, high-confidence identification the wide range of liquids expected to be encountered in a TSA checkpoint environment. Nuclear relaxation data alone (e.g. $T_1$ and $T_2$) are inherently ambiguous and generally do not offer highly accurate liquids identification. Cost, physical footprint, and compatibility with TSA CONOPS are also issues requiring further resolution with low-field relaxation approaches.

While nuclear relaxation data, is useful for gross-order characterization of certain liquids, it is insufficient for complete and unambiguous determination of threat vs. benign liquids. At least two published theoretical investigations Mauler, J., et al, *Identification of Liquids Encountered in Carry-on-Luggage by Mobile NMR*, Springer Science and Business Media B.V., p. 193, 2009, and Kumar, S., et al, *Screening sealed bottles for liquid explosives*, SPIE Vol. 2934, pp. 126, 1997, have shown that relaxation data, if used alone, is indeterminate as to exact liquid identification. Mauler concludes that "Identifying liquids based on relaxation data is possible only with certain restrictions, for instance the number of liquids must be limited" (p. 203), and Kumar asserts (p. 126) that "An ideal system would use high-resolution MR spectroscopy capable of resolving chemical shift spectra to distinguish all liquids with complete reliability." In light of the fact that the variety of known threat liquids and liquid-powder threat mixtures numbers in the hundreds, and that the total number of liquids/liquid mixtures challenging a screening checkpoint potentially numbers in the tens of thousands, this prior research indicates that a robust technology capable of accurate liquids identification over a large range of categories must be developed and employed.

Additionally, liquid samples can be altered, potentially causing the current generation of relaxation technology to be deliberately "spoofed", allowing threat liquids to be masked as benign materials. Recent research conducted by the inventor hereof has shown that a variety of threat liquids can be cloaked or and made to resemble benign liquids (e.g. water) with respect to their relaxation behavior. Physical-chemical properties can be similarly altered and do not offer a unique "fingerprint" for accurate; high-confidence liquids identification. These findings impact the efficacy of the current generation of low-field relaxometry technology as a security screening instrument, unless a discriminating liquid parameter can be found.

Furthermore, the low magnetic fields employed require significant instrument shielding in order to be unperturbed by simple background magnetic interference, such as the Earth's magnetic field. This shielding increases the instrument's physical footprint and cost, and also creates certain operator limitations and restrictions that are difficult to practically achieve in an airport setting (airports are inherently "noisy" magnetic field environments). Devices employed in many low-field systems must be cooled to within a few degrees of absolute zero which requires frequent charging and filling with liquid helium—an added operational expense and logistical challenge. In addition, system stability, instrument drift and other calibration issues have been encountered during the development of low field relaxometry methods.

All publications referred to herein are incorporated herein by reference to the extent not inconsistent herewith.

Accordingly, it is desirable to provide a method and apparatus capable of overcoming the disadvantages described herein at least to some extent.

SUMMARY OF THE INVENTION

Low-field relaxometry offers the advantage of being able to detect and measure data from liquids inside metal containers (because of the low magnetic field employed and hence low Larmor frequency), but suffers from the fact that the $T_1$ and $T_2$ relaxation data obtained does not uniquely identify the liquid. High-field NMR approaches, on the other hand, provide differentiated spectra that can uniquely identify the liquid, but have the drawback that the high frequency radio frequency (RF) (resulting from the high magnetic field employed) cannot penetrate through metal containers.

In contrast, the new "medium-field" (MF) NMR approach herein where the field is sufficiently low that the fields and resulting signals (and required RF pulses) can penetrate the metal container with adequate strength to be usefully employed in gathering spectral data, and at the same time the field is sufficiently high so that the spectral data obtained is high quality and uniquely identifies the liquid examined. The MF approach also significantly reduces cost, simplifies operation and minimizes the equipment required.

Accurate liquids scanning is accomplished with MF-NMR techniques, which include Fourier transform and spectral identification technology. This is done by increasing the measurement magnetic field several hundred-fold (over low-field relaxometry) to a moderate-field design (e.g. 4 MHz, which corresponds to a static magnetic field of 940 gauss) which enhances the first-order relaxation methods currently employed, but the magnetic field is kept low enough so that the contents of metal containers can also be scanned. Application of NMR pulse sequence techniques at these moderate measurement fields can recover unique chemical shift and scalar-coupling information that assists in uniquely determining molecular structure and liquid identity. This approach converts time-domain relaxation data into frequency-domain spectra where detailed magnetic resonance chemical shifts and spectral peak patterns are obtained and signal processing/pattern recognition methods are applied to uniquely fingerprint and specify the liquid.

The inventor hereof has shown that a variety of threat liquids can be chemically cloaked or camouflaged to resemble benign liquids (e.g. water) with respect to their relaxation behavior. Physical-chemical properties can be similarly altered, and do not offer a unique "fingerprint" for accurate, high-confidence liquids identification. These findings call into question the efficacy of the current generation of low-field relaxometry technology as a security screening instrument. However, efforts to "cloak" or "spoof" liquids to alter their relaxation behavior are detectable in an MF-NMR frequency-domain spectral Fourier transform.

Moreover, transforming the system to a medium-field design eliminates the cost and complications of extensive shielding and cryogenic often associated with relaxometry instruments, thus lowering the capital and operating costs. Foil-lined beverage container, regular soda cans and thick-metal containers can also be scanned using the methods disclosed herein.

Research into to NMR pulse sequences and near-field RF engineering in metal containers has demonstrated that MF-NMR technology is applicable to the needs of the Department of Homeland Security (DHS) and the Transportation Security Administration (TSA) for adaptation to an airport bottled liquid scanning device for screening carry-on liquids in a wide array of common commercial containers made of metals, including non-ferrous metals and discriminate between benign and harmful (threat) liquids.

The present invention eliminates the physical constraints of extensive shielding and supercooling, and reduces the footprint of the unit to practical tabletop dimensions. The spectral pattern recognition techniques provided herein allow definitive operator-assisted "threat/no-threat" determinations in a busy checkpoint environment.

Provided herein is a method for analyzing the contents of a liquid in a non-ferrous metal container. The term "analyzing" includes discriminating "benign liquids" from "threat liquids" and can also include identifying components of the liquid. The method comprises:
 a. providing an NMR spectrometer and an NMR probe configured to accept at least a portion of the container;
 b. positioning the container or a liquid-containing portion of the container within a data collection region of the NMR probe;
 c. establishing a homogeneous static medium-strength magnetic field across the data collection region;
 d. applying a radio frequency to said container high enough to obtain a spectrum that provides sufficient information to analyze the contents of the container, but low enough to provide sufficient penetration into the metal container to create magnetic resonance in the contents of the container;
 e. collecting NMR data and generating a Fourier-transformed NMR spectrum; and
 f. analyzing one or more peaks in the NMR spectrum, thereby analyzing one or more contents of the container.

The method is useful for metal containers having a wall thickness from about 250 microns up to about 3.5 inches, depending on the conductivity of the metal. For metals that are poor conductors such as lead, nickel-chromium and other poor conductors known to the art, the method is useful for containers with thicker walls, and for metals that are good conductors such as silver, gold, aluminum, and copper, the method is useful for containers with thinner walls.

Containers suitable for scanning by the methods hereof are any containers, metal or non-metal. However the method is especially useful method for scanning metal containers. Such containers can be selected from the group consisting of foil-lined containers such as foil-lined juice containers, foil-lined beverage containers, and foil-lined baby formula containers, soft-drink cans, beer cans, and aluminum water bottles.

In embodiments, the container is a sealed container.

A medium-strength static magnetic field has a strength between about 250 and about 1500 gauss. The radio frequency range used with this magnetic field is between about 1 and about 6 megahertz. In embodiments, the radio frequency is about 4 megahertz. Pulsed frequencies or continuous swept radio frequencies can be used in a range that matches the resonances of the components desired to be analyzed. When the radio frequency matches the resonances of the components, this helps to identify the components.

The contents of the container can be any liquid, e.g., consumable liquids, benign liquids, which are harmless liquids such as beverages, lotions, toiletries, baby formulas, breast milk, pharmaceutical solutions and the like, or threat liquids such as flammable materials, flammable materials, components of explosives, and/or precursor liquids of explosives (liquids that can be mixed to make explosives). Acetone, hydrogen peroxide, gasoline, alcohol and acids are examples of threat liquids. The methods hereof utilize parameters that can discriminate between components of threat liquids and benign liquids via their Fourier-transform spectra.

Also provided herein is an apparatus for carrying out the methods described above comprising an NMR spectrometer, an NMR probe connected to said spectrometer positioned to hold or a liquid-containing portion of said container within a data collection region of said probe; a medium-strength static magnetic field generator positioned to penetrate at least a liquid-containing portion of said container with a medium-strength magnetic field; a pulsed or continuous swept radio frequency generator positioned to irradiate a liquid-containing portion of said container with a selected range of radio frequencies wherein said radio frequencies corresponds to the medium static field resonance frequencies of the components being tested for, such that the liquids being tested are excited and undergo nuclear resonance, and wherein the selected range of radio frequencies is sufficiently high to provide enough information to discriminate benign liquids from threat liquids.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

Figure 1:
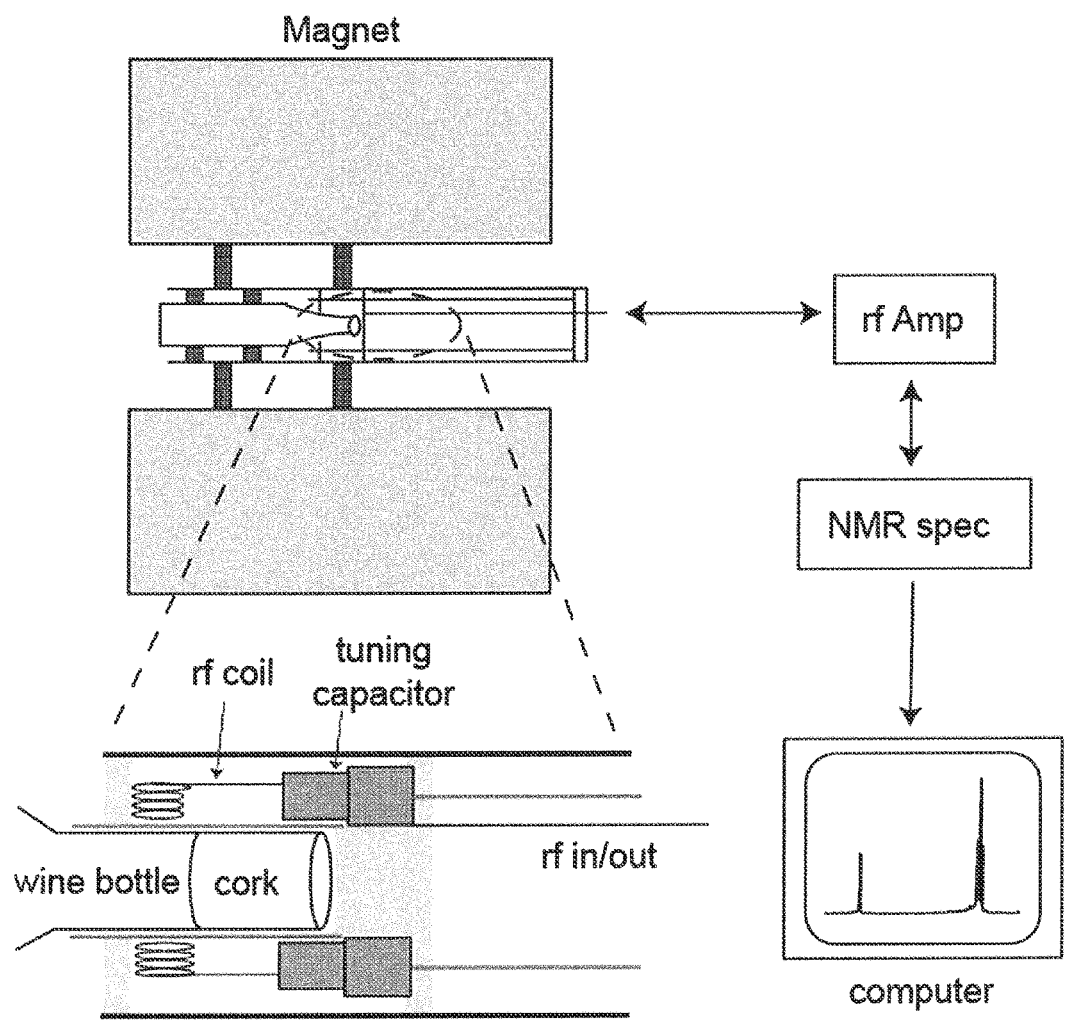
FIG. 1. View of the commercial embodiment of the full beverage (wine) bottle scanning instrument.

NMR spectroscopy is one of the most powerful tools available to identify and study the structure of molecules in solids, liquids, and gases with unprecedented precision. The non-invasive and non-destructive aspects of radio frequency NMR spectroscopy have been exploited to develop the field of magnetic resonance imaging (MRI) for medical purposes, and have been applied by the respondents to closed-container analysis for over six years.

NMR technology disclosed herein has been developed to a commercial level to identify acetic acid and other spoilage contaminants in whole bottles of rare collectible wine where maintaining the original bottle cork and seal is critical to preserving the bottle value. The method is equally applicable to many other types of sealed liquid containers, and in no way affects the quality of the contained food or beverage. The technique is extremely sensitive, detecting down to 50 mg/L acetic acid in a whole (750 mL) bottle of wine, even though the accepted spoilage limit of acetic acid in wine is roughly one hundred times higher.

Technology for scanning whole, sealed-container nuclear magnetic resonance (NMR) principles is currently being commercially applied as a whole bottle, non-invasive method specialized to the analysis of fine and collectable rare wines in their original bottles; some bottles are valued in the thousands of dollars. Using this technology, the bottle is not opened, and the wine is not affected in any manner. A non-technical/non-scientific operator can be fully qualified to operate the detection system with about 6-12 hours of training, and several people have been trained, including a wine sommelier. See U.S. Pat. Nos. 6,911,822, 7,012,427, and 7,339,377.

Wine collectors are interested in monitoring the spoilage that can occur in cellared wine during storage, and must know the condition of the wine, without opening the bottle, with respect to the concentrations of in-vitro chemical compounds that can develop during aging due to elevated storage temperatures and/or oxidation. The whole bottle NMR technique can detect and identify liquid chemical compounds with extreme sensitivity down to trace quantities. To date, it has been used in the chemical characterization and certification of thousands of screened bottles of fine collectable wine.

High-Field NMR technology for closed-bottle wine analysis was successfully applied to the detection of home-made liquid explosives precursor components in enclosed beverage containers (wine bottles) with a >90% probability of detection and a low (negligible) false alarm rate (FAR). The data clearly demonstrates the applicability of this commercial off-the-shelf COTS technology to discriminate benign liquids (drinks, lotions, pharmaceutical solutions, etc.) from those that are potentially harmful and pose a threat (e.g. acetone, peroxide, gasoline, etc.). COTS equipment was modified to screen a wider range of container shapes and sizes to detect potentially harmful liquid chemical compounds, especially explosives and flammable liquids with an adequate per hour throughput rate is achieved in a commercial-scale scanner under anticipated commercial conditions.

EXAMPLES

A simple, low-cost experimental set-up and has been effective in reproducing non-metal SOC container liquids data generated on a low-field relaxometry unit.

Medium field (MF) experiments on foil-lined stream-of-commerce (SOC) containers (e.g. juice boxes) have yielded strong spin echo signals. Detailed, resolved spectra are derived from these spin echoes from which liquids are identified (see below).

Detailed Rabi-cycling experiments on the MF unit show that static fields with Larmor frequencies in the ca. 4 MHz range produce clear free decay (FID) signals through 25 μm aluminum foils with acceptable distortion and predictable field strengths, and are in excellent agreement with near-field theory.

Computer simulations of randomized molecular spectra demonstrate that even liquids with fairly weak J-coupling (e.g. <10 Hz), and with modest chemical shifts (e.g. <5 ppm) produce resolvable spectra through metal containers, uniquely identifying liquids.

Near-field shielding models predict a much lower diminution and degradation of RF signals as they pass through metal than originally thought to be the case. Earlier researchers had apparently employed "far-field" techniques that yielded far greater estimates of field attenuation, but application of near-field models to the MF-NMR case shows that field attenuation is actually much lower than initially thought due to near-field effects.

Example 1

High Field Home-Made Explosives (HME) Studies

A modified version of the high-field NMR technology for closed-bottle wine analysis was successfully applied to the detection of home-made liquid explosives precursor components in enclosed beverage containers (wine bottles) with a >90% probability of detection and a low (negligible) false alarm rate (FAR). The data from this initial test clearly demonstrates the applicability of this COTS technology to discriminate benign liquids (drinks, lotions, pharmaceutical solutions, etc.) from those that are potentially harmful and pose a threat (e.g. acetone, peroxide, gasoline, etc.). The whole bottle instrument configured to study a variety of wine bottle types can be easily modified with COTS equipment to screen a wider range of container shapes and sizes to detect potentially harmful liquid chemical compounds, especially explosives and flammable liquids, with an adequate per hour throughput rate in commercial-scale scanners under the anticipated commercial conditions.

The method uses the full bottle NMR instrument and probe head as shown for the commercial embodiment of the technology in FIG. 1. Here, a single frequency NMR spectrometer delivers rf pulses to an NMR probe head mounted inside of a room temperature, ca. one-foot (310 mm) diameter bore superconducting solenoid magnet. The full, intact and closed bottle is horizontally housed inside of the NMR probe head as shown by the exploded view in FIG. 1. After termination of the rf pulse, the sampled liquid inside the bottle emits a low-voltage rf signal that is mixed to audio frequencies and digitized by the NMR spectrometer to produce a spectrum that directly reflects the different chemical environments of the hydrogen atoms that constitute the chemical compounds in the bottle.

Preliminary HME Detection Trial Results

An initial trial was conducted to determine if the commercial wine-analysis, whole bottle (high-field) NMR technology could be applied to detecting and distinguishing HME explosive precursors and flammable liquids (gasoline, hydrogen peroxide, glycerin, etc.) from benign liquids (drinks, lotions, contact lens solutions, etc.). The results of this trial are highly applicable to MF-NMR. In the course of performing this study, special effort was made to minimize the analysis time, remove screening limitations, and minimize the overall physical dimensions of the instrument while keeping the safety of the operator in mind. Since the current commercial instrument is configured for scanning wine bottles, the trial involved having a non-specialized technician screen HME compounds and benign toiletries and other commercial liquids concealed in wine bottles. Results from this initial "blind test" were excellent, even for container-within-a-container "Trojan horse" attempts to hide a smaller container of, say, pure acetone inside a bottle filled with Gatorade.

Figure 2:
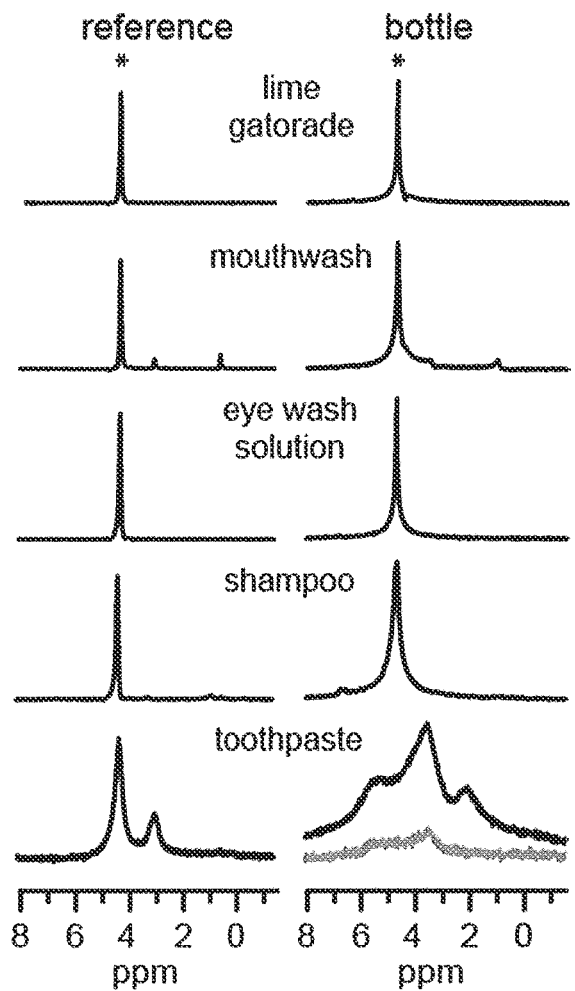
FIG. 2. Reference and full bottle spectra for a collection of benign samples.
Figure 3:
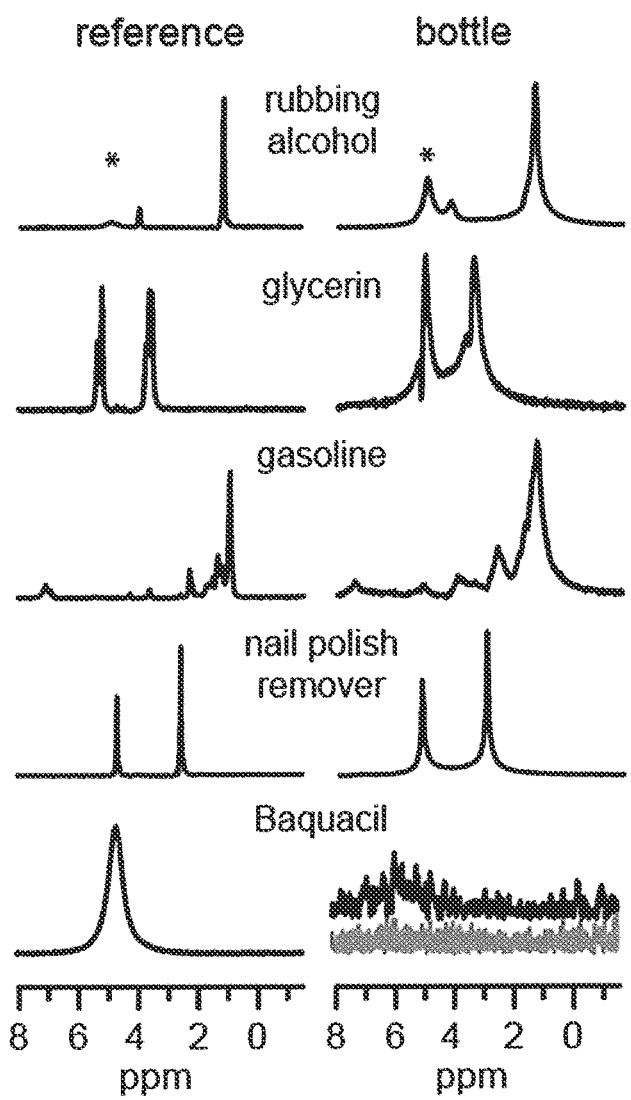
FIG. 3. Reference and full bottle spectra for a collection of flammable/explosive samples.

The sensitivity of the whole bottle NMR technology is outstanding. In FIGS. 2 and 3, NMR spectra from the application of the technology to ca. 1 mL reference samples and ca. 1 L whole bottle containers respectively corresponding to common toiletries and potential explosive compounds are presented. The clear differentiation of peaks between benign and flammable/explosive samples demonstrates the ability of the technology to discriminate between common materials and those potentially employable in the synthesis of explosive or incendiary materials. Reference and sealed bottle NMR results for a subset of benign liquids (lemon-lime Gatorade, mouthwash, eyewash solution, and shampoo), flammable/explosive liquids (rubbing alcohol, glycerin, gasoline, nail polish remover, and Baquacil), and liquid-like substances (toothpaste) are shown. The similarity between the reference (small sample in a 5 mm diameter×5 cm long cylindrical tube) and the sealed container samples (a standard corked 750 mL wine bottle) demonstrates that the measured results do depend on the sample container, but rather on the container contents. Subtle differences between the reference and the sealed bottle results are due to the of different brands of consumables; specifically, the reference and sealed containers used slightly different commercially available brands to demonstrate stability of the method. It is clear from a comparison of the spectra shown in FIG. 2 to those shown in FIG. 3 that there are more profound differences between the spectra for the benign and flammable/explosive compounds. Specifically, most benign substances generally contain large amounts of water. Water produces an NMR peak at 4.7 ppm as indicated by the asterisks in FIGS. 2 and 3. Combining this knowledge with a closer inspection of the spectra shown in FIGS. 2 and 3 shows that one basic earmark for a flammable/explosive liquid is either the absence of water and/or the presence of additional chemical compounds with concentrations comparable to, or in excess of, water. Baquacil, a commonly available source of 28% hydrogen peroxide (one of the precursors for triacetone triperoxide (TATP) and hexamethylene triperoxide diamine (HMTD)), yields one peak indicating the presence of water, but the difference in peak width in comparison to that for the water peak in the benign sample spectra can be used quickly, and non-invasively, to identify the substance as a "threat". Similar line width changes are observed for salt like explosives such as lead azide dissolved into water.

Figure 4:
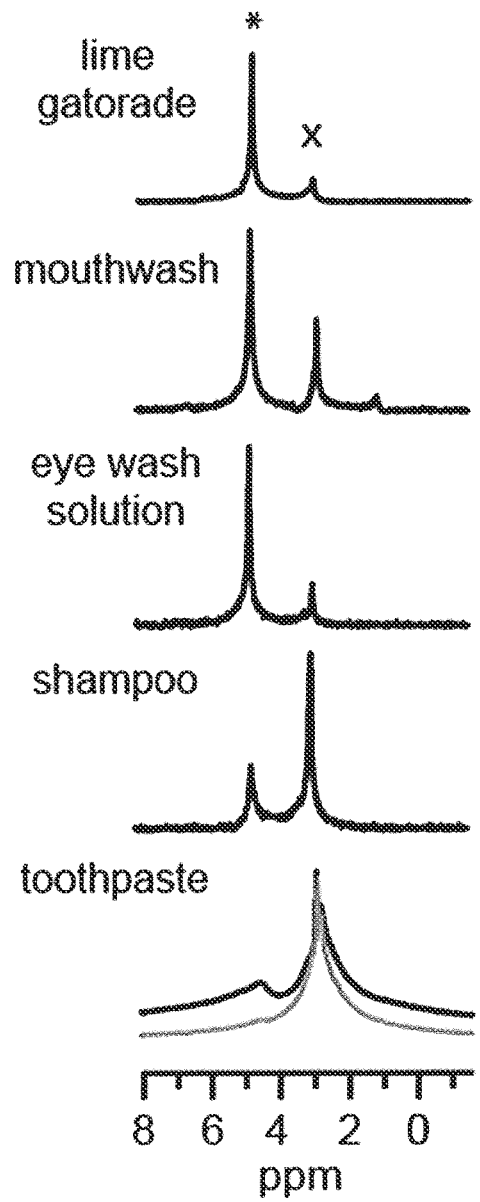
FIG. 4. Full bottle spectra for a collection of "Trojan horse" samples wherein a threat liquid was embedded inside a benign liquid.

The sensitivity of the NMR method is further exploited in FIG. 4 where the whole bottle NMR technique easily detected attempts to conceal banned substances inside of sample containers holding benign compounds. In this example, a tube of the flammable compound acetone was placed into containers of benign liquids in a deliberate attempt to conceal the acetone inside the allowed liquids. Again, the water peak is indicated by an asterisk, while the 2.2 ppm acetone peak is clearly visible and marked by the "x" on the spectra shown in FIG. 4. This peak is also present in nail polish remover since acetone is the active ingredient in this product, as is clearly evidenced in the NMR spectrum in FIG. 3. The spectra shown in FIG. 4 demonstrate that the method is capable of identifying concealed liquid threats.

For the application of this technology to TSA screening, automated spectral analysis is performed by a computer to create a practical approach for an airport scanner manned by TSA personnel. A "red light/green light", "threat/no-threat", or "re-inspect/pass" capability is achieved using COTS spectral analysis software. In a practical airport scanner, the liquid materials presented by passengers to TSA personnel for scanning in their original containers produce a unique NMR "fingerprint" evident from the NMR spectral peaks. This information is compared to a computer-stored data library and digitally identified (the library is constantly updated to match threat-stream information). An alarm is automatically triggered for the ISA scanner-operator if any scanned compound was not registered in the data library, or if unidentifiable by the technology. Back-up Universal Product Code (UPC) coding and comparison adds another level of assurance to the identification effort.

Analysis time. The current commercial process is designed to detect trace quantities of contaminants in three-quarter liter wine bottles while being handled very slowly and gently (lowered slowly into the device). Because of the lack of such handling constraints, the current commercial configuration can process up to one bottle per minute. Using a rapid mechanical slide and COTS automated spectral analysis software, this throughput rate is able to meet TSA volume requirements.

Screening limitations. The method cannot be used for containers made of ferromagnetic materials including steel or "tin" canisters. All containers made of plastic (e.g. polyvinylchloride, polyethylene), glass, or non-ferromagnetic metal materials (e.g. aluminum, copper, non-magnetic materials) can be screened using the high-field NMR technology.

Physical dimensions and power requirements. The total scanner dimensions are approximately 1 m×1 m×2 m (3 ft×3 ft×6 ft.) and it weighs 500-1000 lbs, or roughly the size and weight of a conventional airport X-ray scanner. Standard 120 VAC/15 AC house power is required.

Safety concerns. The whole bottle, high-field NMR screening technology meets all applicable safety standards for safe operation for a UL 913 Class I, Division 2 location where any ignitable or flammable liquids or vapors would exist in a closed container, and in which the circuit under intended operating conditions of the equipment, is not capable, under the test conditions specified, of igniting the specified gas or vapor. Search Results Federal Hazards of Electromagnetic Radiation to Ordnance (HERO) requirements relating to the activation of electro-explosive devices (EED's) are followed, and full rf attenuation measures implemented to eliminate any fixed-beam hazard. Compliance requirements for the static magnetic field are typical of many other types of devices, including medical devices (MRI); appropriate magnetic shielding and a modest stand-off distance may be required for TSA settings. No electronic equipment or magnetic storage devices (e.g. computers, PDA's, credit cards, video film) should pass-through the scanner, or come within a defined stand-off perimeter.

Example 2

Medium-Field NMR

Figure 5:
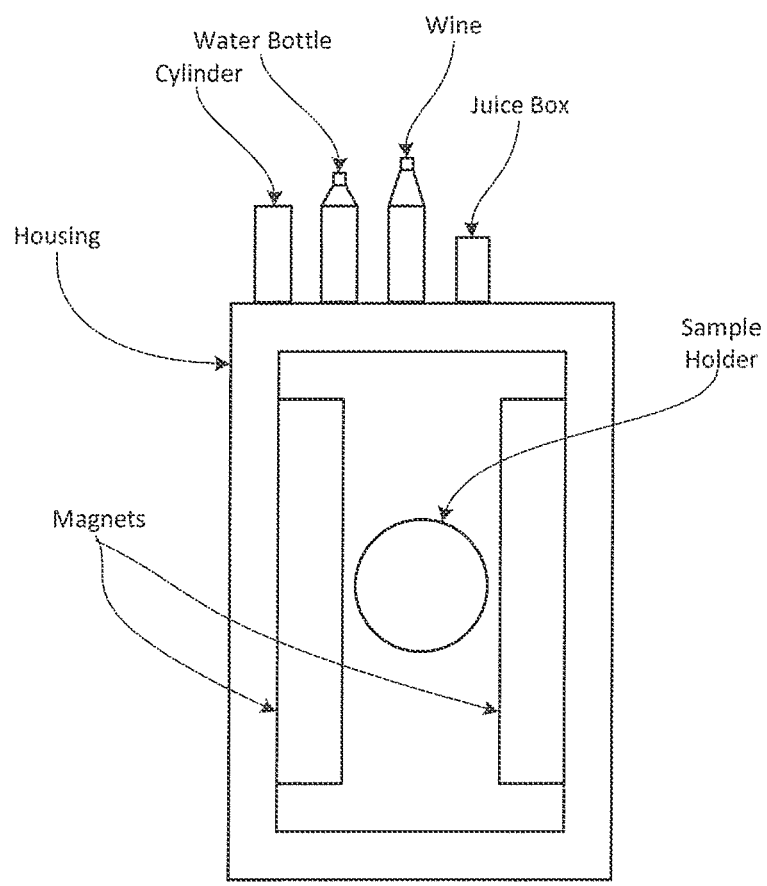
FIG. 5. Block diagram of a 940 G electromagnet along with assorted sample containers used in the Medium-Field NMR study.
Figure 8:
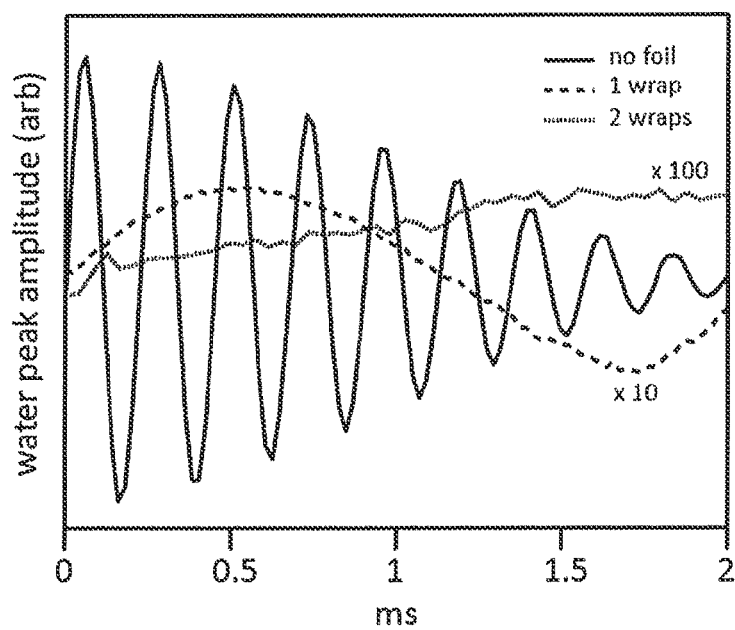
FIG. 8. Rabi cycling results in both the non-metal wrapped PTFE tube, and the two aluminum-wrapped PTFE containers by delivering 130 W power to the NMR probe. The thick black, the dashed, and thin gray lines respectively correspond to measurements obtained using the plain PTFE tube, the PTFE tube wrapped with 1 layer of foil (25 microns), and 2 layers of foil (50 microns), respectively.
Figure 9:
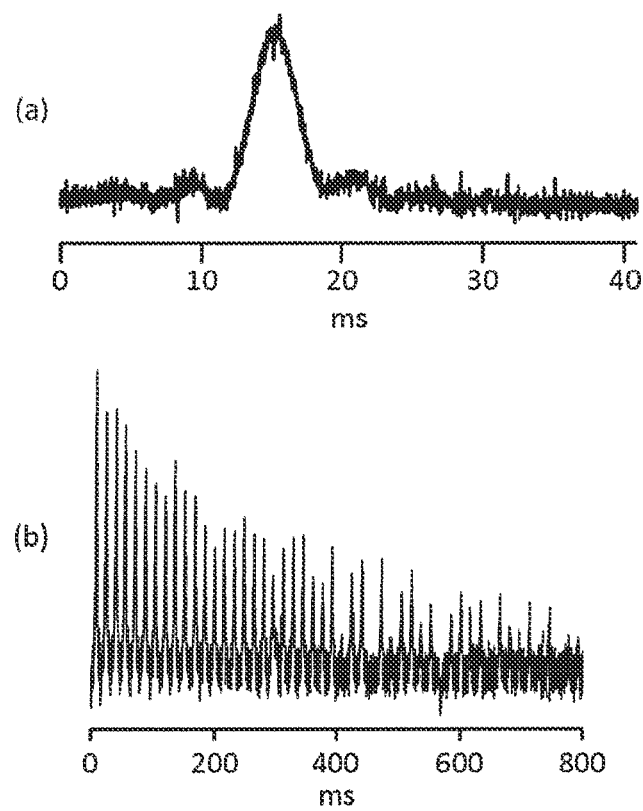
FIG. 9. Spin echo signals obtained from an Al shielded 50 mL PTFE centrifuge tube in (a) and a SOC Al shielded juice box in (b).
Figure 10:
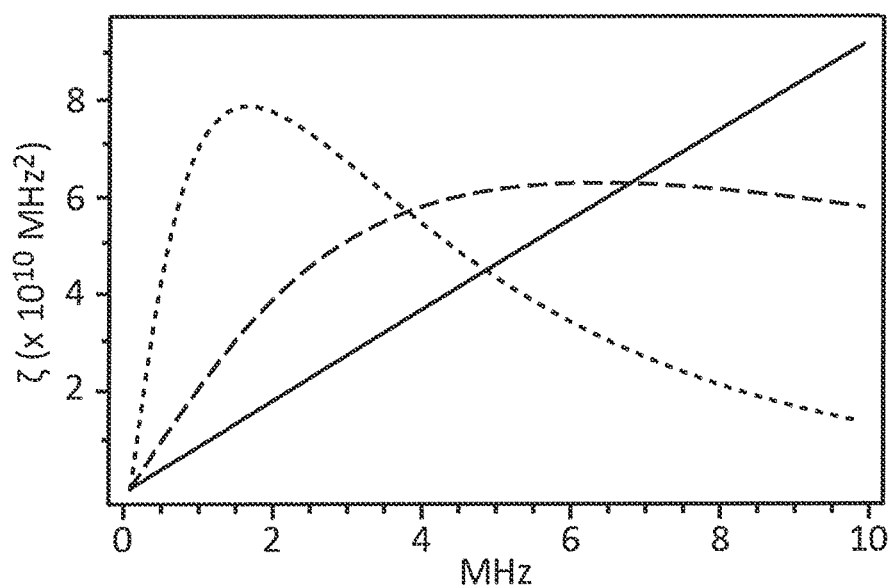
FIG. 10. ζ values for a cylindrical conducting shell for Δ=25 μm (solid line), 100 μm (dashed line), and 200 μm (dotted line) thick aluminum shield. This figure describes the optimal frequency for generation of adequate NMR spectra of liquids contained in aluminum metal containers. From the figure it can be seen that the optimal frequency for penetration into and for obtaining adequate spectra into a 200-micron-thick aluminum container containing water is just below 2 megahertz, whereas for an aluminum container of 100 micron thickness the optimal frequency is seen to be to be about 5 megahertz. All containers studied are cylindrical aluminum containers and they are completely embedded in a solenoidal probe with the axis of the aluminum container cylinder is coincident with the axis of the solenoid.
Figure 11:
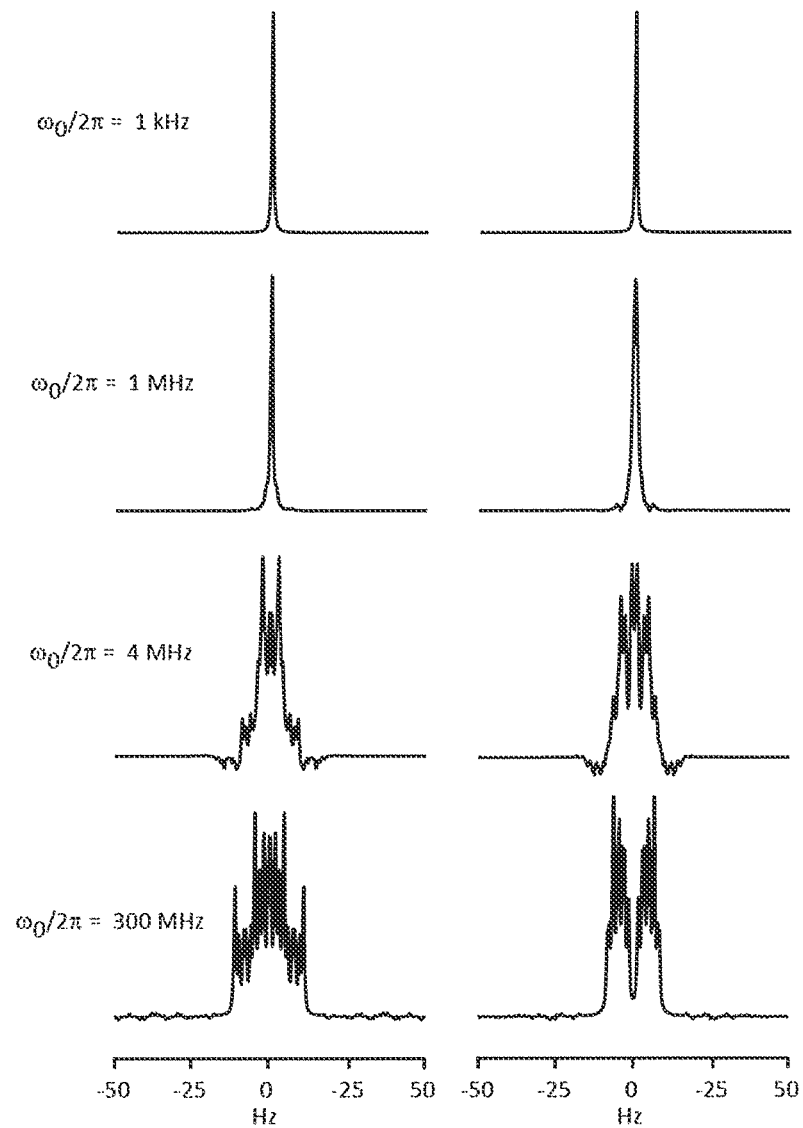
FIG. 11. Simulations of the Fourier transform of the transient echo signal obtained from two different four spin systems with randomly chosen chemical shifts between 0 and 5 ppm and randomly chosen J couplings between all of the spins between 0 and 10 Hz. The static magnetic field and hence the Larmor frequency increases from top to bottom as indicated in the graphic. This figure demonstrates that a medium field of a value between 1 and 4 megahertz (corresponding to between 250 and 1000 gauss) is adequate to produce an identifiable Fourier transform spectrum to discriminate between two liquids. But as seen in the previous figure, this field can penetrate aluminum containers up to 200 microns in thickness, thus proving the value of the invention.

An experimental set-up for testing metal, foil-covered or foil-lined containers at a medium 4 MHz measurement field was completed, tested and commissioned. Photographs of the electromagnet employed for these measurements are provided in FIG. 5. Spectra were obtained using this surplus instrument built from "spare" parts and using simple induction coils. A progressive; stepwise protocol involving a 50 mL polytetrafluoroethylene (PTFE) centrifuge tube initially not covered with foil, then covered with one foil layer (25 □m), then two foil layers (50 μm), etc., was implemented to gain critical insight into the impacts of metal on rf pulses and NMR signals. Clear NMR signals for water in the PTFE centrifuge tubes without foil and with one 25 μm thick foil layer are shown in FIGS. 8 (a) and (b) respectively. Critically important Rabi cycling experiments were conducted to investigate the detailed impact of metal on rf input and NMR signal output (FIGS. 9 and 10). Additionally, excellent spin echo data was obtained from liquids in metal foil containers (FIG. 11). Finally, data from 30% $H_2O_2/H_2O$ solutions in a 12 oz plastic bottle permitted a comparison of the relaxation parameters of water and peroxide solution that is consistent with the data recorded in ultra-low relaxometry setups.

Metal Container Description. Experiments were performed in three types of containers: A plain (unwrapped) 50 mL PTFE centrifuge tube, and two 50 mL PTFE centrifuge tubes wrapped with 1 layer of aluminum foil (25 μm), and two layers of aluminum foil (50 μm), respectively. The Al foil wrapped tubes are used to probe NMR signal dependence on metal thickness through Rabi cycling experiments. In a second set of experiments; the surface eddy currents are studied by tracking the NMR signal intensity from a water filled PTFE centrifuge tube (with one aluminum foil layer) as a function of the angle between the long axis of the tube and the long axis of the rf coil. The angular dependence of the NMR signal strength in the conducting container for fixed rf pulse length was further studied by interrupting the conducting foil in various locations.

Figure 7:
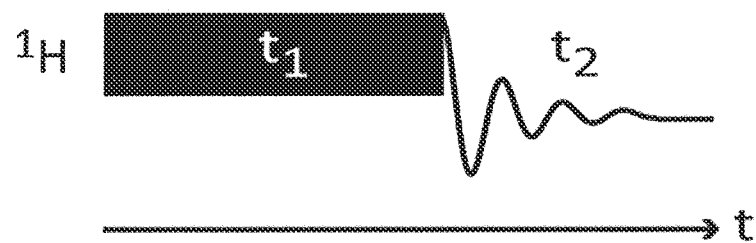
FIG. 7. Pulse sequence used to obtain Rabi cycling transients. Separate $^1$H NMR spectra are recorded in the time domain $t_2$ for different rf irradiation times $t_1$.

Moderate-Field (4 MHz) Experiments in Aluminum-Wrapped Tubes. A series of Rabi cycling experiments were conducted using the three containers described above to determine the effects of the metal foil on cycling frequency and damping rate and thus attempt a preliminary evaluation of the impact of metal on rf excitation and signal detection. A Rabi cycling experiment consists of placing the various sample-loaded containers into the static magnetic field (940 G) followed by application of high power rf to the tuned and matched rf coil for a time $t_1$. After the pulse was turned-off, the receiver aperture was opened and the free induction decay signal measured. A graphic of this simple pulse sequence is shown in FIG. 7. The maximum amplitude of the Fourier transform of this free induction signal or spectrum as a function of rf excitation time $t_1$ is shown in FIG. 8 for all three containers.

Figure 6:
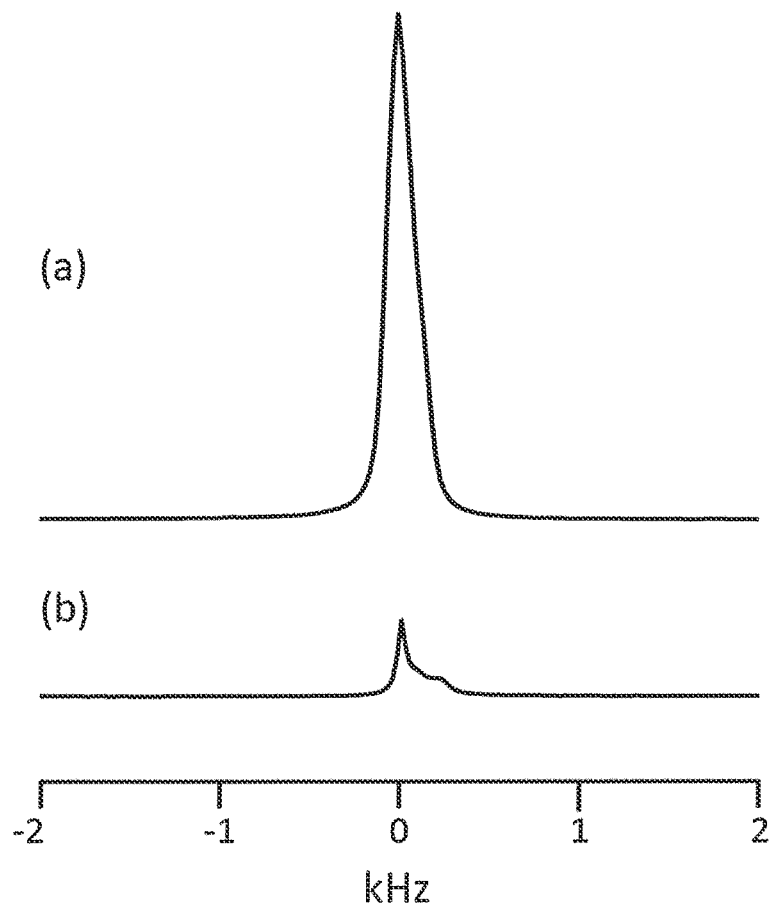
FIG. 6. Representative $^1$H NMR spectra obtained at a 4 MHz $^1$H Larmor frequency for a water-filled 50 mL PTFE centrifuge tube without (a), and with (b), 25 μm aluminum foil shielding.

The Rabi cycling experiment provides an accurate measure of the nutation angle generated for a given pulse length $t_1$ and fixed rf magnetic field strength $\omega_1$. The angle of rotation around the rf magnetic field in a rotating frame of reference at resonance is $\omega_1 t_1$. As expected, longer pulses cause the nutation angle to "cycle" to increasingly larger values. Decoherence and signal damping is clearly present in these interferrograms due to inhomogeneous rf characterized here by the rotating frame line width parameter $T_R^*$. Values for the Rabi frequency $\omega_1$ and the rotating frame line width parameter $T_R^*$ are obtained by fitting the data shown in FIG. 10 to the function $\sin(\omega_1 t_1)\exp(-t_1/T_R^*)$. The damping parameter is measured by fitting the oscillation maxima to an exponentially decaying curve. The cycle time in the interferrograms shown in FIG. 8 yields the Rabi frequency, which in the case of the maximum ca. 130 W rf power used in this particular study for a plain tube (no foil) is $\omega_1/2\pi=4.29$ KHz. Table 1 summarizes the Rabi frequency $\omega_1/2\pi$, the maximum amplitude, and the rotating frame line width parameter $T_R^*$ for the three different containers (all loaded with water). Based upon the data shown in Table 1, the time to rotate a z-directed magnetization into the x-y plane or the $\pi/2$ rf pulse time is $t_{\pi/2}=\pi/2\omega_1=58$ μs for the sample without Al shielding, a number that increases by about an order of magnitude to ca. 600 μs for one shielding layer. The effect of the metal shielding on the overall NMR linewidth is minimal as shown in FIG. 6 where half width at half maximum is ca 130 Hz=$1/T_2^*$. From the spectra obtained in metal containers, the line width $1/T_2^*$ is comparable to the Rabi frequency $\omega_1/2\pi$. In normal high field NMR experiments, $\omega_1/2\pi$ is typically at least two orders of magnitude larger than the line width (e.g. the non-shielded container) and it is known that such a difference must be present in order to generate a full amplitude spin echo signal, experience that dictates that more rf power is needed to increase the nutation rate $\omega_1$ and concomitantly decrease $t_{\pi/2}$.

TABLE 1

Summary of Rabi cycling experiments in plain (non-metal) and metal-wrapped PTFE tubes

| Foil layers (thickness) | Rabi Freq $\omega_1/2\pi$ | Calculated S.E. | Predicted Rabi Freq. | Observed Amplitude | Predicted Amplitude | Damping rate $1/T_R^*$ |
|---|---|---|---|---|---|---|
| 0 (0) | 4.29 KHz | N/A | N/A | 29,064 | N/A | 813 Hz |
| 1 (25 μm) | 417 Hz | 20 dB | 417* Hz | 1441 | 275 | — |
| 2 (50 μm) | 125 Hz | 26 dB | 215 Hz | 93 | 73 | — |

Spin Echo Experiments. Regardless of magnetic field strength applied, heterogeneities introduced by container end effects, sample shape, and presence of a conducing metal container will substantially warp/spoil the inherent homogeneity of the field. It is for this reason that the pulse sequences involving the recovery of both heteronuclear and homonuclear J couplings are considered. The necessary building block of these sequences is the formation of a $\pi/2$–$\tau$–$\pi$ spin echo, a signal that modulates at these J coupling frequencies (for molecules other than water) as a function of the time $\tau$. Indeed the recovery of such a modulated spin echo is substantially easier at moderate to high magnetic fields than at lower fields. The consequence of this symmetry breaking by the magnetic field is the exclusive recovery of homonuclear J couplings, an effect that can only be reproduced in low field through use of a dilute $^{13}$C nucleus and an effect that automatically scales the already small low field signal by ca. a factor of 100. Spin echoes have been observed in both prepared (aluminum shielded PTFE centrifuge tubes) and COTS containers as shown in FIG. 9. FIG. 9(a) shows just one spin echo ($\tau=15$ ms and $t_{\pi/2}=500$ μs) obtained from the PTFE tube shielded with one layer of aluminum foil while the train of echoes shown in FIG. 9(b) for an aluminum coated juice box corresponds to increasing T in 15 ms steps.

Optimal Field Strength. The ability to screen liquids in sealed non-ferrous, metallic containers with moderate field NMR spectroscopy reflects four basic parameters; three are design parameters, one is based on the molecular physics of the liquid, and all four are intimately related to magnetic field strength. These parameters are: (1) penetration of an rf magnetic field through the ca. 25-100 thick metal container, (2) the size of the nuclear spin magnetization (proportional to the static field strength), (3) the efficiency of inductive/Faraday detection, and (4) the ability of the static magnetic field to break the low field scalar J coupling isotropy and thus generate J-coupling modulated echo signals. The first key design criterion relating to rf penetration into conducting shells was thoroughly addressed through calculations of the rf shielding effect SE as a function of frequency. Combining these results with the fact that the size of the nuclear spin magnetization and the efficiency of inductive detection scale linearly as $M_0 = Nh\omega/2 kT$ and EMF $\propto \omega$ where $\omega=\gamma H$ respectively, suggest that the size of an NMR signal for a precessing magnetization $|M| \propto M_0$ inside of a conducting container is given by:

$$\zeta = \omega^2 10^{-\frac{SE}{20}}$$

It is important to note that the usual $\omega^2$ detection efficiency is recovered when the shell is removed as SE=0 in that case. FIG. 10 shows the detection efficiency $\zeta$ for the infinitely long cylindrical aluminum shell for three different choices of thickness $\Delta$. The solid, dashed, and dotted lines in FIG. 10 correspond to $\Delta=25$ μm, 100 μm, and 200 μm respectively. The dashed $\Delta=100$ μm curve is likely appropriate for most SOC conducting containers (e.g. cans) and the maximum at ca. 5 MHz is consistent with the ca. 4 MHz operating frequency anticipated on J coupling recovery calculations. Indeed there is a tradeoff between the three design parameters, but true optimization must also consider the ability of the spin echo to measure homonuclear J couplings. Examples of this final point are provided in FIG. 11. The synthesized molecular spectra in FIG. 11 correspond to four J-coupled spins with four different chemical shifts and pertain to four different realizations of the static magnetic field corresponding to Larmor frequencies of $\omega/2\pi=1$ kHz, 1 MHz, 4 MHz, and 300 MHz. It should be clear from the plots in this figure that a Larmor frequency of 4 MHz or higher is sufficient to resolve J-coupled spectra if J<10 Hz and $\sigma$<5 ppm for the J coupling and shift parameters, reflecting the values of these parameters in real molecules detectable by MF-NMR.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for analyzing the contents of a liquid in a non-ferrous metal container, said method comprising:
   a. providing an NMR spectrometer and an NMR probe configured to accept at least a portion of the container, wherein said metal container has a wall thickness up to about 3.5 inches (poor conductor lead, nickel-chromium) good conductor would be max 250 microns, silver, gold, aluminum, copper;
   b. positioning the container or a liquid-containing portion of the container within a data collection region of the NMR probe;
   c. establishing a homogeneous static medium-strength magnetic field across the data collection region;
   d. applying a radio frequency to said container high enough to obtain a spectrum that provides sufficient information to analyze the contents of the container, but low enough to provide sufficient penetration into the metal container to create magnetic resonance in the contents of the container;
   e. collecting NMR data and generating a Fourier-transformed NMR spectrum; and
   f. analyzing one or more peaks in the NMR spectrum, thereby analyzing one or more contents of the container.

2. The method of claim 1 wherein said metal container has a wall thickness up to about 250 µm.

3. The method of claim 1 wherein said container is a sealed container.

4. The method of claim 1 wherein said medium-strength static magnetic field between about 250 and about 1500 gauss.

5. The method of claim 1 wherein said radio frequency is between about 1 and about 6 megahertz.

6. The method of claim 1 wherein said radio frequency is about 4 megahertz.

7. The method of claim 1 wherein said container is selected from the group consisting of foil-lined containers, soft-drink cans, beer cans, and aluminum water bottles.

8. The method of claim 1 wherein said contents comprise benign liquids and threat liquids.

9. The method of claim 8 wherein said benign liquids are selected from the group consisting of beverages, lotions, toiletries, baby formulas, breast milk, and pharmaceutical solutions.

10. The method of claim 8 wherein said threat liquids are flammable materials, components of explosives and/or explosive precursor liquids.

11. The method of claim 8 wherein said threat liquids are selected from the group consisting of acetone, hydrogen peroxide, gasoline, and acids.

12. The method of claim 1 wherein said radio frequency is high enough to discriminate between components of threat liquids and benign liquids via their Fourier-transform spectra.

13. A method for analyzing the contents of a liquid in a non-ferrous metal container, said method comprising:
   a. providing an NMR spectrometer and an NMR probe configured to accept at least a portion of the container, wherein said container is a sealed container;
   b. positioning the container or a liquid-containing portion of the container within a data collection region of the NMR probe;
   c. establishing a homogeneous static medium-strength magnetic field across the data collection region;
   d. applying a radio frequency to said container high enough to obtain a spectrum that provides sufficient information to analyze the contents of the container, but low enough to provide sufficient penetration into the metal container to create magnetic resonance in the contents of the container;
   e. collecting NMR data and generating a Fourier-transformed NMR spectrum; and
   f. analyzing one or more peaks in the NMR spectrum, thereby analyzing one or more contents of the container.

14. The method of claim 13 wherein said metal container has a wall thickness up to about 250 µm.

15. The method of claim 13 wherein said medium-strength static magnetic field between about 250 and about 1500 gauss.

16. The method of claim 13 wherein said radio frequency is between about 1 and about 6 megahertz.

17. The method of claim 13 wherein said container is selected from the group consisting of foil-lined containers, soft-drink cans, beer cans, and aluminum water bottles.

18. The method of claim 13 wherein said contents comprise benign liquids and threat liquids.

19. The method of claim 18 wherein said threat liquids are flammable materials, components of explosives and/or explosive precursor liquids.

20. The method of claim 18 wherein said threat liquids are selected from the group consisting of acetone, hydrogen peroxide, gasoline, and acids.

* * * * *